(12) United States Patent
Schweikert et al.

(10) Patent No.: US 7,856,745 B2
(45) Date of Patent: Dec. 28, 2010

(54) INFORMATION CLIP FOR FLEXIBLE TUBING

(75) Inventors: Timothy Schweikert, Levittown, PA (US); Kenneth J. Chesnin, Philadelphia, PA (US); John Stephens, Perkiomenville, PA (US); Kevin Sanford, Chalfont, PA (US)

(73) Assignee: Medical Components Inc., Harleysville, PA (US)

( * ) Notice: Subject to any disclaimer, the term of this patent is extended or adjusted under 35 U.S.C. 154(b) by 247 days.

(21) Appl. No.: 11/895,051

(22) Filed: Aug. 22, 2007

(65) Prior Publication Data

US 2008/0051731 A1 Feb. 28, 2008

Related U.S. Application Data

(60) Provisional application No. 60/839,913, filed on Aug. 24, 2006.

(51) Int. Cl.
G09F 3/00 (2006.01)
(52) U.S. Cl. ............................... 40/316; 40/658; 40/660
(58) Field of Classification Search .................. 40/316, 40/666, 660; 251/9, 10; 604/250; 174/112; 439/491; D13/157
See application file for complete search history.

(56) References Cited

U.S. PATENT DOCUMENTS 497,594 A * 5/1893 McGrady ..................... 40/647

(Continued)

FOREIGN PATENT DOCUMENTS

GB 2042131 9/1980

(Continued)

OTHER PUBLICATIONS

International Report on Patentability dated Mar. 5, 2009; PCT/US2007/018657 (8 pages).

(Continued)

Primary Examiner—Lesley Morris
Assistant Examiner—Kristina Staley
(74) Attorney, Agent, or Firm—Anton P. Ness; Fox Rothschild LLP

(57) ABSTRACT

Information-bearing articles (10,50,100,100',150, . . . 850) for securing to flexible tubing (38) such as catheters and their extension tubes, to provide important information about the tubing (38) such as flow rating or contraindications on types of cleaning fluid not to be used therewith. The devices are provided with large outwardly facing indicia-bearing surfaces (30,32;70,72;120,122; . . . 834) and may be clipped directly to the tubing (38) at a selected location therealong, or be clipped directly to a clamp member (40,330) that is disposed along and around the tubing for clamping the tubing (38) when desired to occlude fluid flow therethrough. Those devices (10,100,100',550, . . . 750) clippable to the tubing may have a C-shaped channel (18,20,58,108,554,604) therealong that may be flexed open to be placed about the tubing, which may be temporarily compressed as well to enter the channel, or the devices may be rings (800,850) that clip closed about the tubing (38). Other devices (200,250, . . . 500) are adapted to be clipped to the clamp (40,330) by latch projections (208,210;258,260; . . . 508,510). Still others (50, 150) may be clipped to the tubing (38) but be adapted to be placed partially around an end or a side of the clamp (40,330).

30 Claims, 19 Drawing Sheets

U.S. PATENT DOCUMENTS

| | | | |
|---|---|---|---|
| D31,083 S | 6/1899 | Seng | |
| 1,580,649 A | 4/1926 | Christiansen | |
| 2,094,796 A | 10/1937 | Kahn | |
| 2,894,056 A | 7/1959 | Bogese | |
| 3,068,600 A | 12/1962 | Blanchet | |
| 4,256,132 A | 3/1981 | Gunter | |
| 4,261,121 A * | 4/1981 | Coon | 40/332 |
| 4,378,648 A | 4/1983 | Loof et al. | |
| 4,429,852 A | 2/1984 | Tersteegen et al. | |
| D273,993 S | 5/1984 | Schulte et al. | |
| 4,497,124 A | 2/1985 | Olive | |
| 4,641,443 A * | 2/1987 | Wilmes | 40/316 |
| 4,775,121 A | 10/1988 | Carty | |
| 4,876,810 A | 10/1989 | Piana et al. | |
| 5,027,538 A * | 7/1991 | Wilmes et al. | 40/316 |
| 5,035,399 A | 7/1991 | Rantanen-Lee | |
| 5,138,784 A | 8/1992 | Niwa | |
| 5,170,578 A * | 12/1992 | Pampel | 40/316 |
| 5,203,056 A | 4/1993 | Funk et al. | |
| 5,275,282 A | 1/1994 | Ross et al. | |
| 5,281,228 A | 1/1994 | Wolfson | |
| 5,309,604 A | 5/1994 | Poulsen | |
| 5,316,246 A | 5/1994 | Scott et al. | |
| 5,334,955 A | 8/1994 | Strnad | |
| 5,407,109 A | 4/1995 | Zuckerman | |
| 5,468,022 A | 11/1995 | Linder et al. | |
| 5,593,392 A | 1/1997 | Starchevich | |
| D381,367 S | 7/1997 | Rashman | |
| 5,950,883 A | 9/1999 | Bond et al. | |
| 5,971,436 A | 10/1999 | Cox | |
| 5,974,708 A | 11/1999 | Webb et al. | |
| 6,079,135 A | 6/2000 | Ruiz | |
| 6,089,527 A | 7/2000 | Utterberg | |
| 6,240,668 B1 | 6/2001 | Clawson et al. | |
| 6,335,672 B1 | 1/2002 | Tumlin et al. | |
| D477,776 S | 7/2003 | Pontaoe | |
| 6,651,362 B2 | 11/2003 | Caveney | |
| D489,452 S | 5/2004 | Schweikert | |
| D491,265 S | 6/2004 | Schweikert | |
| D498,299 S | 11/2004 | Schweikert | |
| 6,823,617 B2 | 11/2004 | Schweikert | |
| 6,929,625 B2 | 8/2005 | Bierman | |
| 2003/0093932 A1 | 5/2003 | Battaglia, Jr. | |
| 2004/0068902 A1 | 4/2004 | Hadzic et al. | |
| 2004/0159024 A1 | 8/2004 | Wortley et al. | |
| 2005/0044759 A1 | 3/2005 | Schweikert | |
| 2005/0277873 A1 | 12/2005 | Stewart et al. | |
| 2006/0015072 A1 | 1/2006 | Raulerson | |

FOREIGN PATENT DOCUMENTS

WO    WO 2005/058410    6/2005

OTHER PUBLICATIONS

International Search Report, dated Jan. 3, 2008; PCT/US2007/018657 (4 pages).

Written opinion, dated Jan. 3, 2008; PCT/US2007/018657 (6 pages).

\* cited by examiner

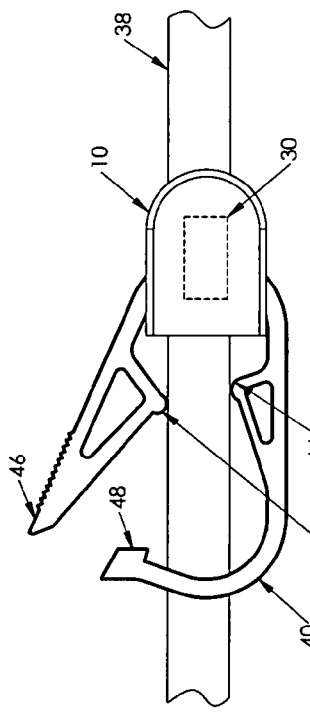
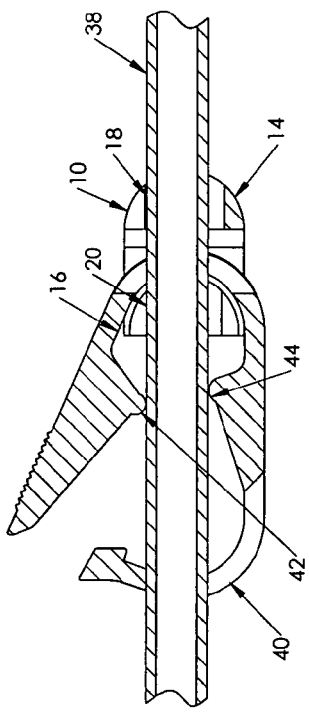
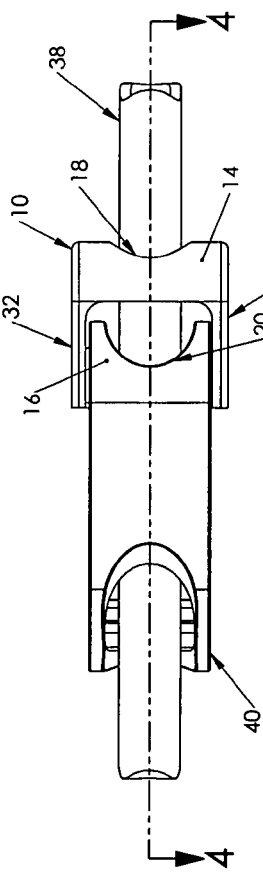
FIG. 3
FIG. 4
FIG. 5

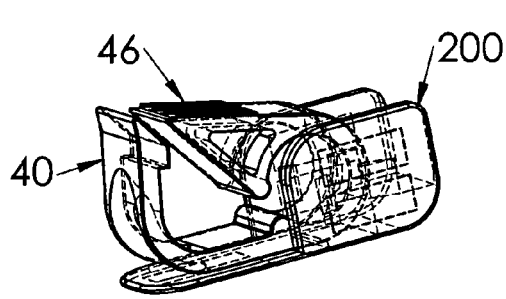
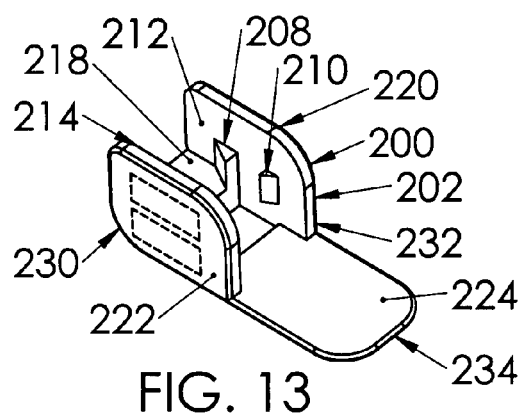
FIG. 17     FIG. 13
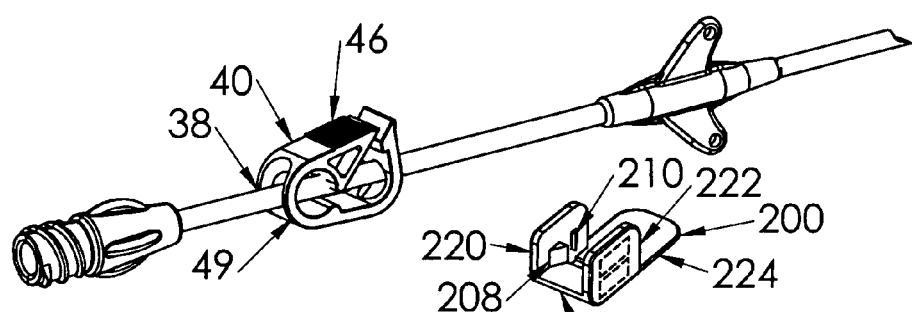
FIG. 14
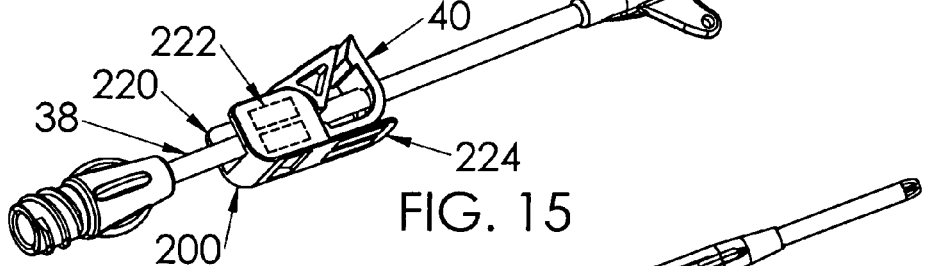
FIG. 15
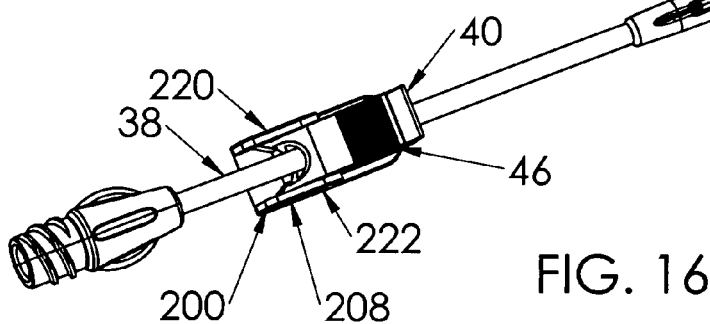
FIG. 16

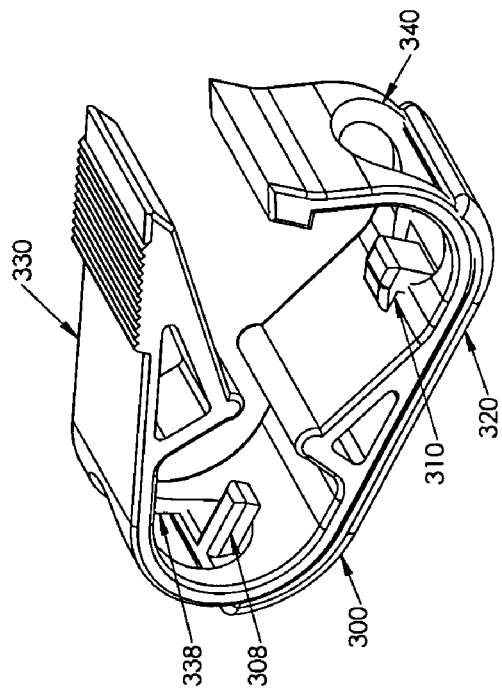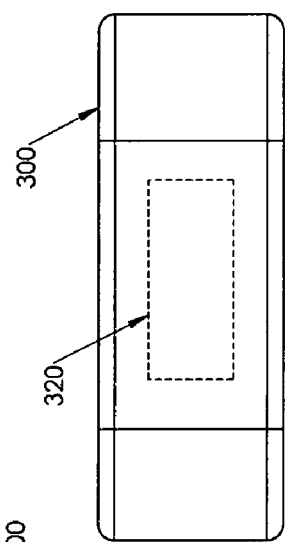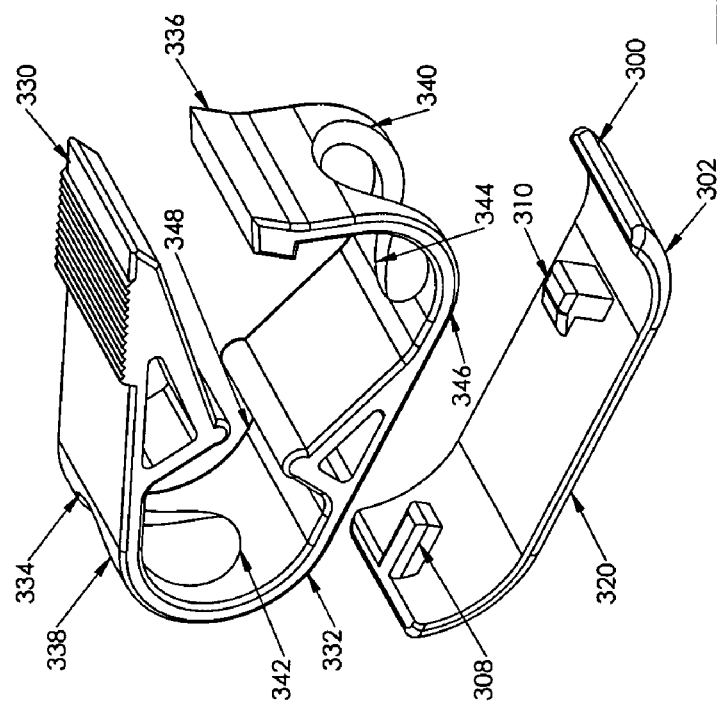
FIG. 21
FIG. 22
FIG. 20

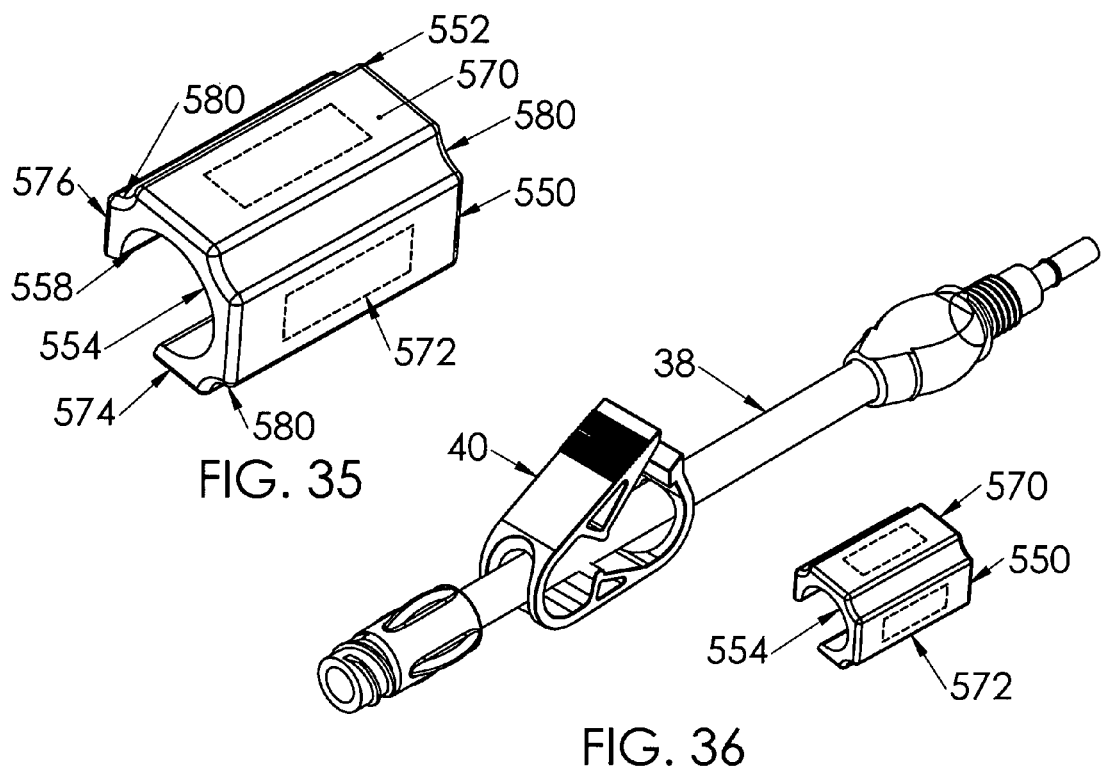
FIG. 35
FIG. 36
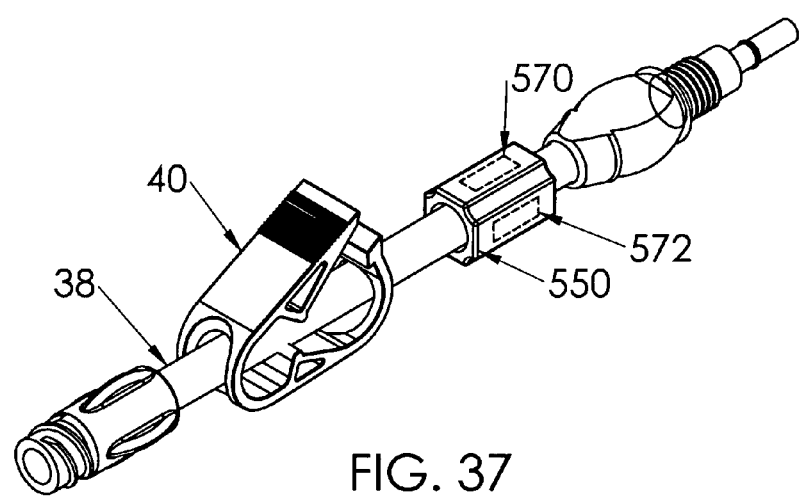
FIG. 37

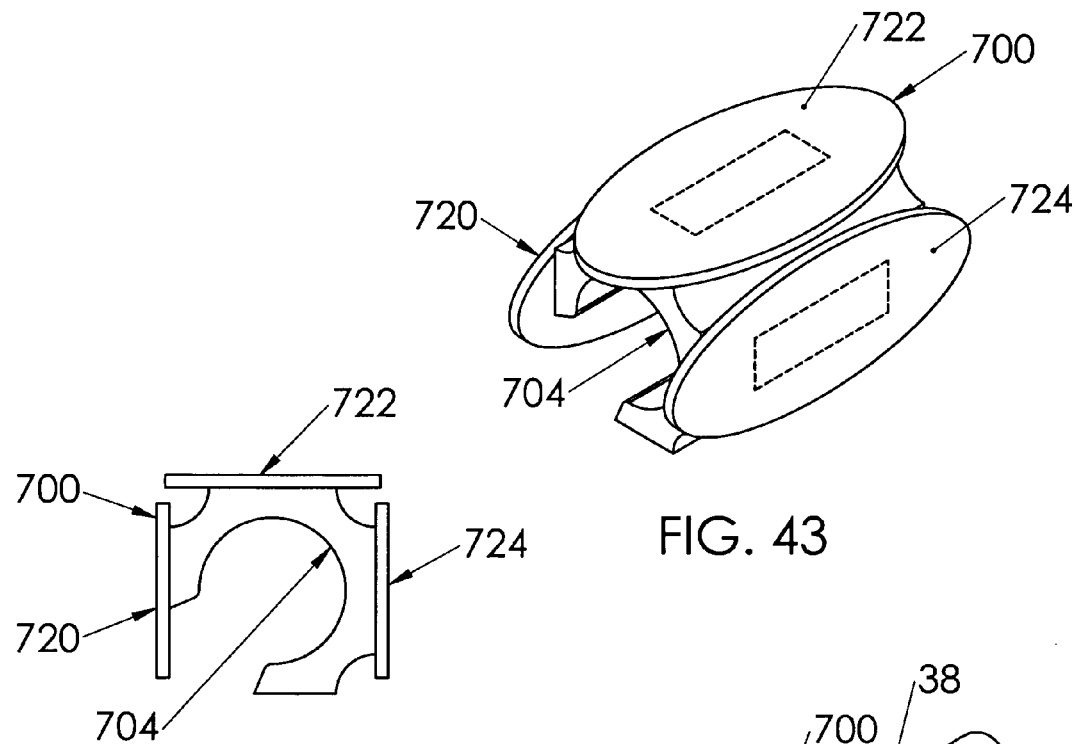
FIG. 43
FIG. 44
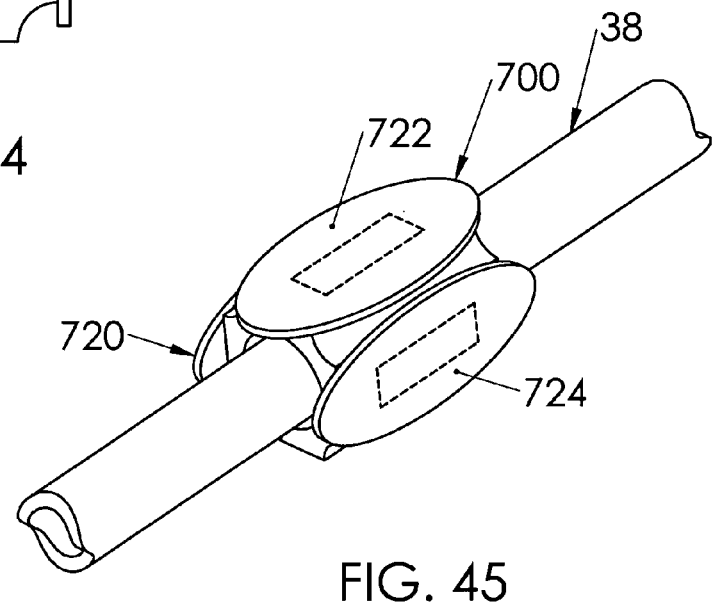
FIG. 45

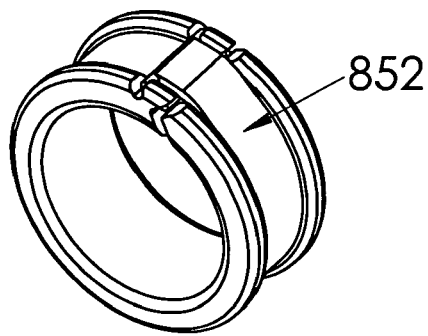
FIG. 54
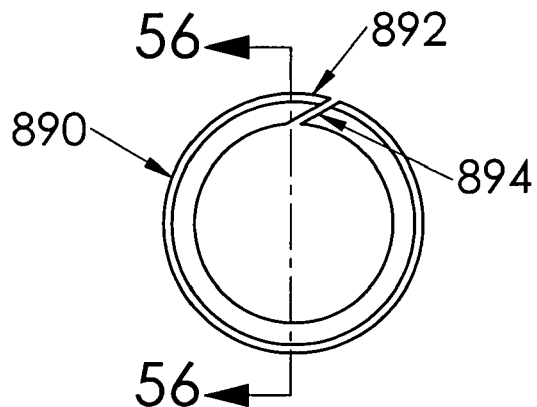 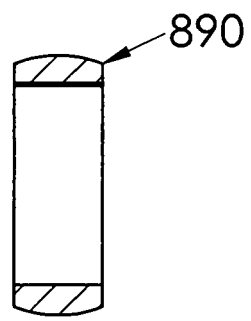
FIG. 55  FIG. 56
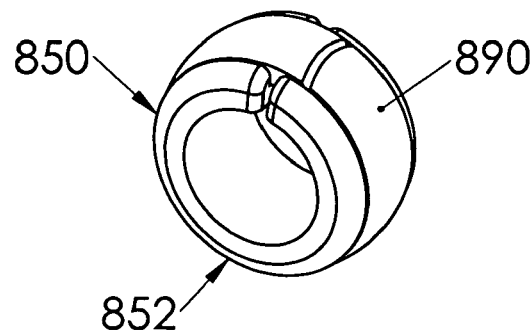
FIG. 57

INFORMATION CLIP FOR FLEXIBLE TUBING

CROSS-REFERENCE TO RELATED APPLICATIONS

This application claims priority from Provisional U.S. Patent Application Ser. No. 60/839,913 filed Aug. 24, 2006.

FIELD OF THE INVENTION

This relates to flexible tubing and more particularly to medical tubing such as catheters and their extension tubes and to information-bearing devices therefor.

BACKGROUND OF THE INVENTION

Catheters for the introduction or removal of fluids may be located in various venous locations and cavities throughout the body for the introduction or removal of such fluids. Such catheterization may be performed by using a single catheter having multiple lumens. A typical example of a multiple lumen catheter is a dual lumen catheter in which a first lumen introduces fluids and a second lumen removes fluids. These catheters are very useful for procedures such as hemodialysis, wherein blood is removed from a patient through the first lumen for processing in a hemodialysis machine, and the processed blood is returned to the patient through the second lumen. Alternatively, multiple catheters, each having a single lumen, may be inserted in multiple locations in the patient, such as in each femoral vein.

Catheters are manufactured in different sizes and from different materials depending on the circumstances of their use. For example, smaller catheters are used on smaller patients, and different materials may be used depending on whether the catheter is intended to be in the patient for a short period of time, such as several hours or days, or for an extended period of time, such as weeks or months.

Catheters typically include indicia printed on the extension tubes that provides vital information such as the size, priming volume, and recommended as well as contra-indicated cleaning solutions to use around the catheter entrance to the patient and other information related to care and maintenance of such catheters and extension tubes, and also for intravenous tubing. For example, some cleaning fluids can actually dissolve certain types of polyurethane materials from which some catheters are constructed. Text information is placed on the extension tubes to warn the user not to use such cleaning fluids.

The information printed on the extension tubes may vary depending on the intended catheter use. However, one drawback to this approach is that text size and clarity is limited, since the extension tubes are tubular and are typically translucent. Additionally, the text applied to the extension tubes is susceptible to rubbing off over time. Further, information such as priming volume may be printed on the catheter, such as on the extension tube. If a repair is necessary that requires a luer to be removed and a new, replacement luer installed onto the extension tube, the priming volume has changed, because the extension tube has been shortened as a result of the luer replacement. It would be desirable to provide a replaceable component with the catheter that can indicate the correct priming volume after such a replacement.

U.S. Pat. No. 6,823,617 assigned to the assignee hereof, sets forth an advance over printing of such information directly on the flexible tubing, and discloses an information-bearing article for use with tubing such as a medical catheter and may be used in combination with a tubing clamp. The information-bearing article includes a ring-shaped body having an opening extending therethrough for receipt therethrough of the tubing. At least one of the opposed sides of the article has an enlarged generally planar outwardly facing surface that bears indicia thereon, such as printed or embossed indicia. Certain embodiments disclosed therein may be applied directly onto and along the flexible tubing. Other embodiments are disclosed that are adapted to be used in association with a certain well-known clamp member (a Roberts clamp) and are shaped and dimensioned to be nested within the skeletal structure of the clamp member as well as at least partially around the circumference of that length of flexible tubing extending between ends of the clamp member, and further adapted to permit the clamp member to be manipulated as desired between an unclamping state with respect to the flexible tubing and a clamping state wherein fluid flow through the tubing is occluded.

It is desired to provide an information-bearing article for use with a flexible conduit that is convenient to be placed onto the conduit and convenient to be removed therefrom.

BRIEF SUMMARY OF THE INVENTION

The present invention is directed to information-bearing articles or devices applicable to flexible tubing, particularly to medical tubing such as catheters, extension tubes and intravenous tubing. The inventive devices are easily applied to and are easily removable from the flexible tubing or to clamp members used with such tubing, or both, being assembled from laterally of the tubing or the clamp member. Each inventive device has at least one outwardly facing surface sufficiently large to contain easily readable indicia or information with or without a magnifying component, and preferably has at least two such indicia-bearing surfaces on a body of the device. Each inventive device body also has a connecting section whereby the device is securable directly to and around the flexible tubing and/or to a clamp member that itself is securable directly to and around the flexible tubing.

In one general type of embodiments, the information-bearing devices include a connection section that self-secures or clips directly onto or at least around the flexible tubing without impinging on the fluid flow through the tubing. The connection section is a C-shaped body section having an inner diameter preferably no more than only incrementally larger than the outer diameter of the tubing, and with a side entrance less than the diameter of the flexible tubing, whereby the device or the tubing or both are flexible and temporarily compressible respectively to permit application to the tubing from laterally of the tubing, and removal from the tubing when desired, at a selected location along the tubing. One, and preferably two, three or even four indicia-bearing surfaces may be provided facing outwardly in respective different directions, and the device may be sized to be rotatable around the tubing as desired for better readability.

In another general group of embodiments, the inventive device is particularly adapted to be utilized in conjunction with a clamp member that is secured to and along the flexible tubing. The device is so shaped and dimensioned to at least partially conform to and to be positioned along one or more outer surfaces of the clamp member and includes a connection section that self-secures or clips to portions of the framework of the clamp member and/or a connection section that self-secures or clips to the flexible tubing adjacent to the clamp member, or even within the interior of the clamp member, all in a manner to prevent translation along the tubing away from the clamp member. The device may have one, or two or three indicia-bearing outwardly facing surfaces. With this type of embodiment, the device does not interfere with the operability of the clamp member when it is being activated between clamping and unclamping states with respect to the tubing, and the device further does not impinge on fluid flow through the tubing.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 3 to 5 are a side view, cross-section view and a bottom view of the assembly of FIG. 2, with FIG. 4 taken along lines 4-4 of FIG. 5;

FIGS. 13 to 16 are isometric views of an additional embodiment of indicia-bearing device showing the device, the device spaced from an extension tube assembly, and assembled thereto from the side and from the top, respectively;

FIG. 17 is an isometric view of the device of FIGS. 13 to 16 secured to the clamp member of FIG. 12, with hidden details shown in phantom;

FIGS. 20 to 22 are isometric views and a bottom view of an additional embodiment of indicia-bearing device spaced from a clamp member, and then as secured to the clamp member;

FIGS. 35 to 37 are isometric views of still another embodiment of indicia-bearing device by itself and as secured to a flexible tube of an assembly spaced from a clamp member therealong, with fittings at proximal and distal ends of the tube;

FIGS. 43 to 45 are isometric views of still another embodiment of indicia-bearing device by itself and as secured to a flexible tube;

FIGS. 54 to 57 are views of a further embodiment of indicia-bearing device in isometric view and a magnifying device for use thereon in elevation and cross-section views, and with the magnifying device assembled over the indicia-bearing device in an isometric view.

DETAILED DESCRIPTION OF THE INVENTION

Figure 2:
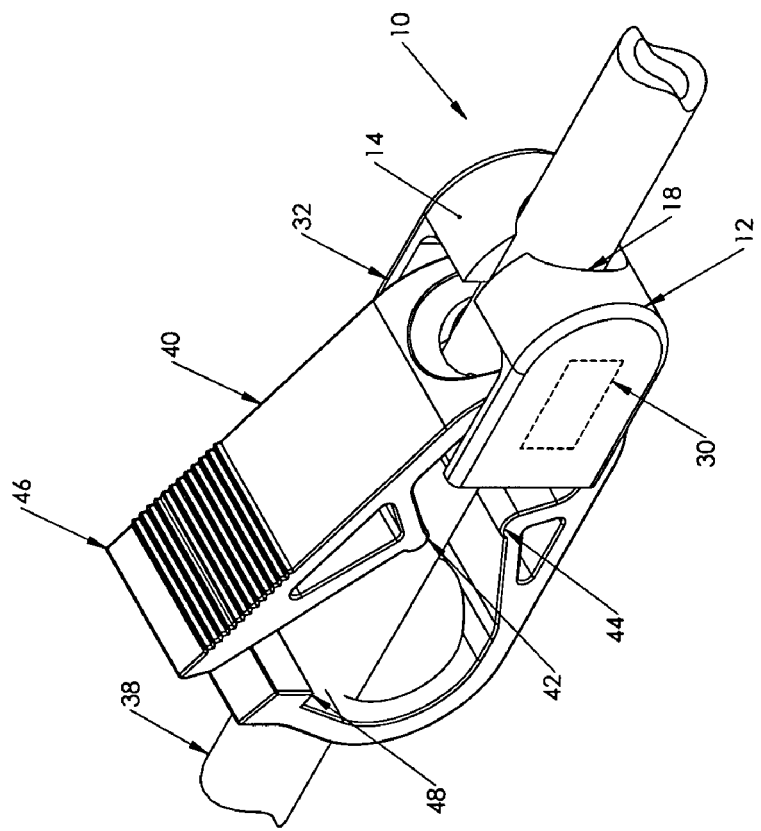
FIG. 2 is an isometric view of the device of FIG. 1 applied to an extension tube adjacent to an end of a clamp member on the extension tube.

In the drawings, like numerals indicate like elements throughout. Certain terminology is used herein for convenience only and is not to be taken as a limitation on the present invention. Flexible tubing or conduit includes catheters and extension tubes therefore, without limitation. The terms "distal" and "proximal" refer, respectively, to directions closer to and away from a catheter to which the extension tube is to be connected for fluid communication therewith by a hub or other connector in an implantable catheter assembly, or closer to and away from the patient in intravenous tubing. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Generally, the indicia-bearing devices of the present invention have a body and provide at least one enlarged outwardly facing indicia-bearing surface and preferably two and up to four such indicia-bearing surfaces, and include a connection section that is adapted to secure the devices either to and along a length of flexible tubing, or to a clamp member secured to and along the flexible tubing or, optionally, to both. Indicia-bearing areas are generally designated throughout the drawings by boxes of dashed lines. Clamp members illustrated herein are of the Roberts type, but the present invention is not restricted to only this type of clamp; modifications may be made to the indicia-bearing article of the present invention to adapt to different styles of clamps, within the skill of the artisan. The device embodiments of FIGS. 1 to 12 are shown to include connecting sections that are adapted to secure to and around the flexible tubing at the location of a clamp member of a flexible tube/clamp assembly, and the device includes at least one portion that is adapted to conform to at least exterior portions of the clamp; in FIGS. 13 to 34, the device embodiments are provided with connecting sections to self-secure directly to the clamp member; and the device embodiments of FIGS. 35 to 57 are shown to include connecting sections that are adapted to secure directly to the flexible tubing independently of any clamp member, especially where the flexible tubing already has fittings affixed to proximal and distal ends thereof, and these embodiments have at least one outwardly facing surface that bounds, or several such surfaces that together bound, at least about three-fourths of the circumference of the tubing, with one or more of these surfaces also bearing indicia. Furthermore, all the embodiments are shaped and dimensioned to maintain a minimum and unobtrusive profile, with all portions thereof remaining adjacent to the flexible tubing and/or the clamp thereon, to minimize patient discomfort and risk of being snagged by fabric, other tubing, wiring and the like, as is greatly desired.

In the first embodiment shown in FIGS. 1 to 5, an indicia-bearing device 10 includes a body 12 and a pair of side walls 30, 32, one on either side of the device and that are joined by the device body 12, each having outwardly facing surfaces that may be indicia-bearing. Also seen in FIGS. 2 to 5 is a length of flexible tubing 38, and a clamp member 40 secured thereto and therealong, the clamp being manipulatable between an unclamping state as shown, and a clamping state (not shown) in which fluid flow through the tubing is occluded. FIGS. 3 and 4 show the sections 42, 44 that would impinge on the flexible tubing for its occlusion with the end of the arm 46 latching to the clamp body at latch 48 to hold it in the clamping state; such a clamp is conventionally known as a Roberts clamp.

Device 10 is provided with first and second transverse connecting sections 14, 16 separated by a clearance 24 that each include a C-shaped channel 18, 20 extending therethrough both being coaligned and parallel to the indicia-bearing surfaces 30, 32 and are such that the device can be applied securely to the flexible tubing 38. The device is of elastomeric material and is moderately flexible so that it temporarily flexes to some degree during application to the tubing, with the flexible tubing being temporarily compressed until the tubing is seated in the C-shaped channel 20 at one location within clamp member 40 and also then coupled similarly at C-shaped channel 18 at another location exterior of clamp member 40, which inhibits translation movement of the device along the tubing away from the clamp. It is seen that the indicia-bearing surfaces 30, 32 coextend along outwardly facing opposite sides of the clamp member and the tubing without interfering with the manipulation of the clamp member between its clamping and unclamping states. The C-shaped channel may comprise a circumference of at least 180° to 360°, and more preferably about from 210° to 330°.

Figure 7:
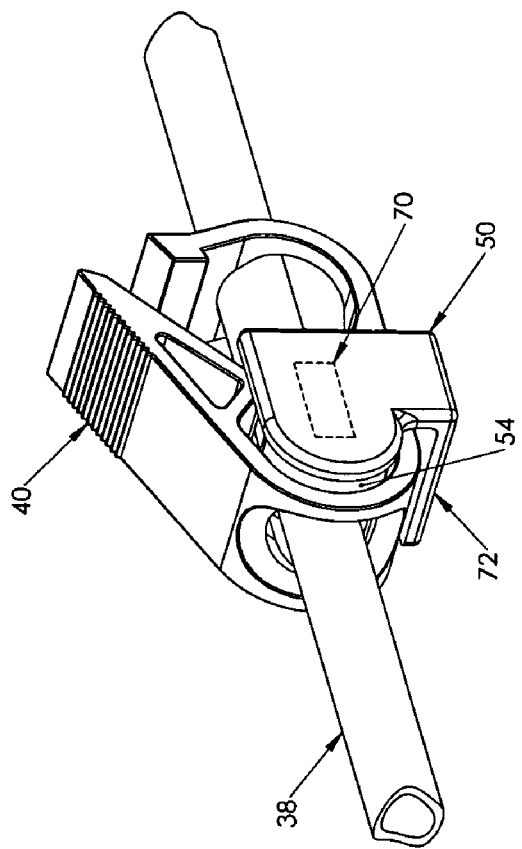
FIGS. 6 and 7 are an isometric view of a third embodiment by itself and as assembled to a flexible tube/clamp assembly.
Figure 6:
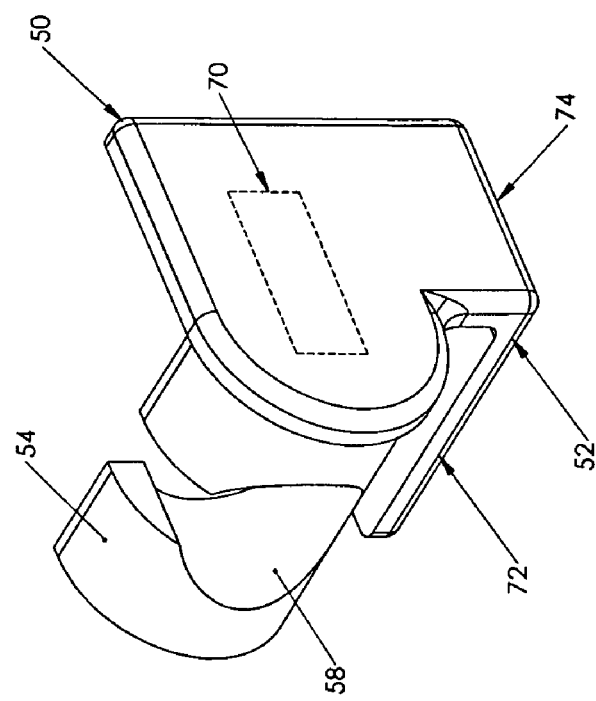

In FIGS. 6 and 7 is shown a second embodiment of indicia-bearing device 50. Body 52 includes a connecting section 54 with a C-shaped channel 58 that is adapted to clip onto the flexible tubing 38 at a location within the clamp 40. Device 50 is shown to have two indicia-bearing surfaces 70,72 with surface 70 eventually being positioned along one side of clamp 40. Surface 72 extends orthogonally from a depending bottom edge 74 of surface 70 to extend transversely under the bottom of clamp 40 and tubing 38 of the tubing/clamp assembly.

Figure 9:
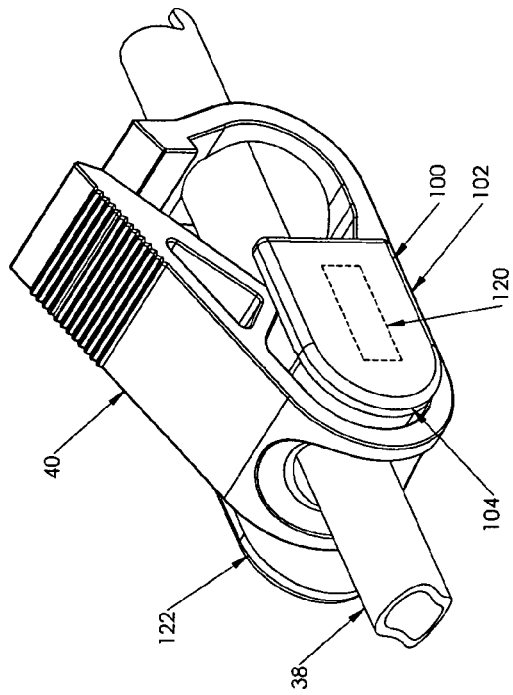
FIGS. 8 and 9 are an isometric view of a fourth embodiment by itself and as assembled to a flexible tube/clamp assembly.
Figure 8:
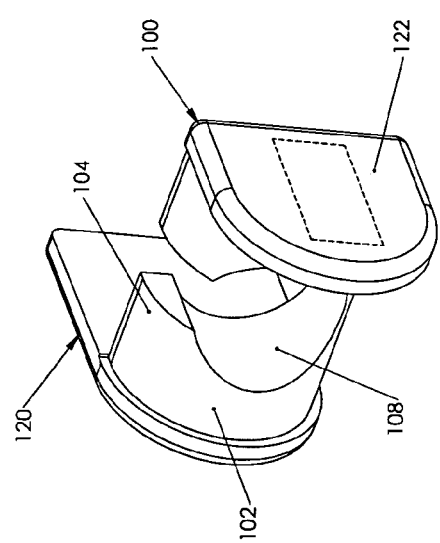

FIGS. 8 and 9 illustrate a third embodiment of indicia-bearing device 100 of the present invention. In device 100, body 102 includes a transverse connecting section 104 defining therethrough a C-shaped channel 108 for enabling device 100 to clip onto the flexible tubing 38 at a location within clamp 40. Device 100 provides a first indicia-bearing surface 120 that extends along one side of clamp 40, while a second indicia-bearing surface 122 extends in the opposite direction from, and on the opposite side of the tubing from, first indicia-bearing surface 120 to extend past an adjacent end of clamp 40 and therebeyond, thus not occluding the view of the length of tubing 38 within clamp member 40. Optionally, the inwardly facing surface of first surface 120 may also be provided with indicia that would be viewable through the clamp and the transparent tubing.

Figure 1:
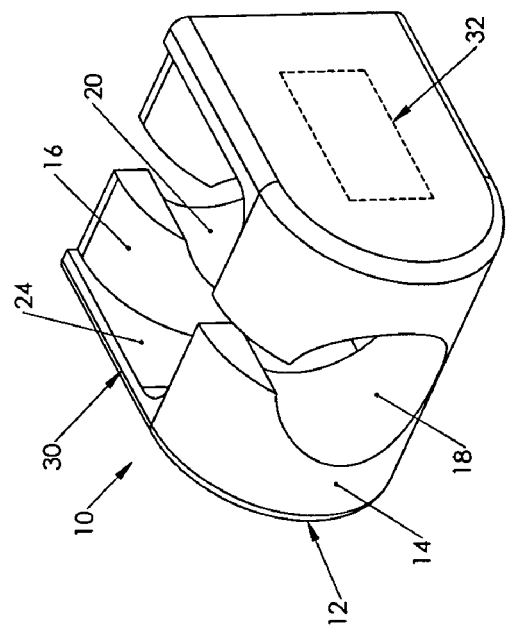
FIG. 1 is an isometric view of a first embodiment of indicia-bearing device of the present invention.
Figure 10:
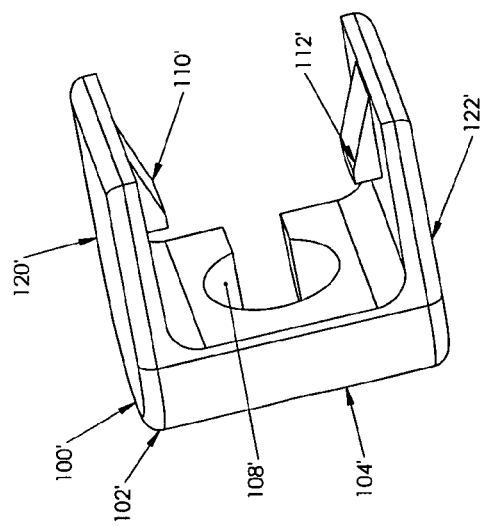
FIG. 10 is an isometric view of a fifth embodiment of device similar to those of FIGS. 1 to 8 and having a pair of latching sections that cooperate with the clamp member.

Another embodiment of device 100' is shown in FIG. 10 that is similar to device 10 of FIG. 1, having a body 102' that includes a transverse section 104' defining a C-shaped channel 108' for clipping around the flexible tubing, and having a pair of side walls defining indicia-bearing surfaces 120', 122'. Additionally, device 100' includes a pair of latch projections 110', 112' extending toward each other from inwardly facing surfaces of the side walls and that are spaced from the transverse section 104' and are adapted to latch behind the framework of the clamp body (see FIG. 2) in order to secure the device 100' against translation along the tubing away from the clamp.

Figure 12:
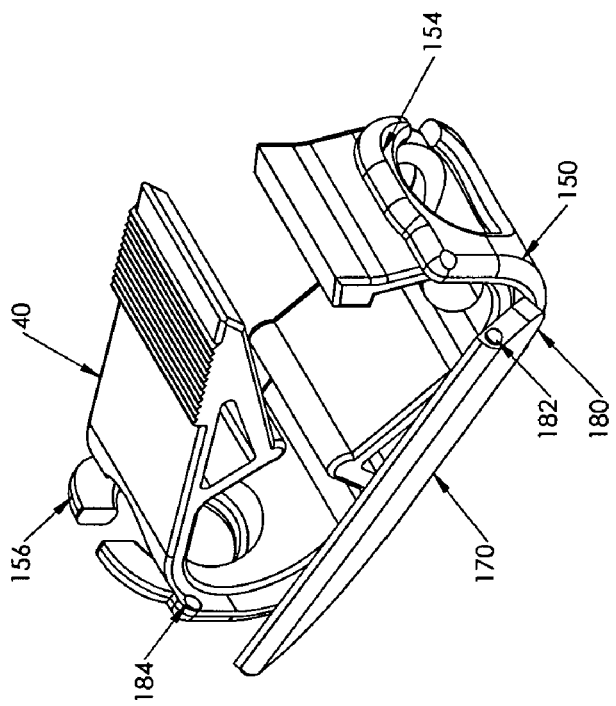
FIGS. 11 and 12 are an isometric view of a fifth embodiment of device by itself and as assembled to a clamp member, with the flexible tube removed to expose detail.
Figure 11:
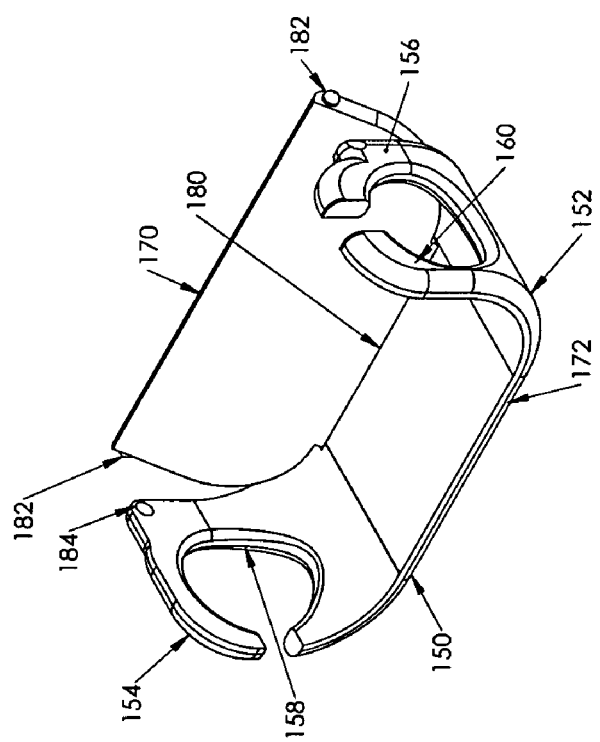

With regard to FIGS. 11 and 12, another embodiment of indicia-bearing device 150 is shown. Body 152 defines first and second transverse connecting sections 154, 156 spaced apart a distance just greater than the length of the clamp member, defining a pair of respective first and second C-shaped channels 158, 160 that are clippable directly onto the tubing at locations beyond both ends of clamp 40 and adjacent thereto. A first indicia-bearing surface 170 is integrally joined to the body at a living hinge 180 and includes detents 182 that snap-fit with respect to corresponding recesses (or holes) 184 at respective ends of body 152 (or at least at one thereof) when rotated into a vertical orientation along one side of clamp 40 orthogonal to a second indicia-bearing surface 172 that comprises a bottom wall or floor of body 152 to underlie the clamp 40. Device 150 does not include portions that extend into the interior of the clamp.

In FIGS. 13 to 17, another embodiment of indicia-bearing device 200 is shown. Device 200 is different from the previously discussed embodiments of FIGS. 1 to 12 in that it is adapted to clip directly onto the clamp 40 rather than onto the tubing 38. Body 202 provides three outwardly facing surfaces 220, 222, 224 having a generally rectangular periphery, where the periphery can also be said to be partially rounded, and that may each be indicia-bearing, with two of the surfaces 220, 222 comprising side walls of body 202 coextending from a transverse section 218 of the body from respective first ends 230 to respective second ends 232. The third indicia-bearing surface 224 extends to a free end 234 from, and joining, second ends 232 of both of the opposing side walls and comprises a third or bottom wall of device 200 that extends along a bottom of the clamp body. Body 202 also includes transverse section 218 extending between and joining first ends 230 of the side walls that define surfaces 220, 222, and also can be said to be disposed along the bottom of device 200. Body 202 includes connecting sections which may be pairs of latch members 208, 210 along inside surfaces 212, 214 of both side walls. The pairs of latch members are spaced slightly apart and near to respective first and second ends 230, 232 of the side walls, and are adapted to latch onto an end 49 of clamp 40 that joins the arm 46 to the remainder of the clamp as the device 200 is pressed upwardly from beneath the clamp 40, or as the device is translated from along the tube 38 toward end 49 of clamp 40, since the side walls of the device are sufficiently flexible to temporarily flex outwardly until the latch pairs are properly positioned on both sides of end 49 thus securing device 200 from any incidental unintentional movement. Also seen in FIGS. 14 to 16 are fittings at both ends of the extension tube, comprising a luer connector (on the left) and a catheter hub (on the right) that joins the extension tube to a catheter.

Figure 19:
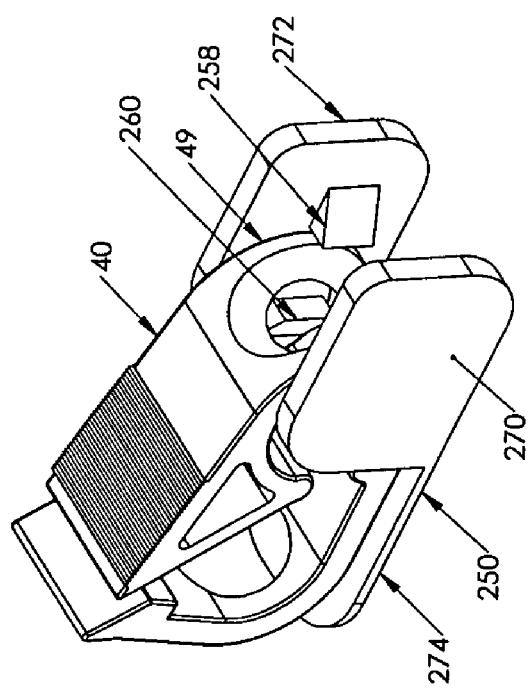
FIGS. 18 and 19 are isometric views of an additional embodiment of indicia-bearing device by itself and as secured to the clamp member of FIG. 12.
Figure 18:
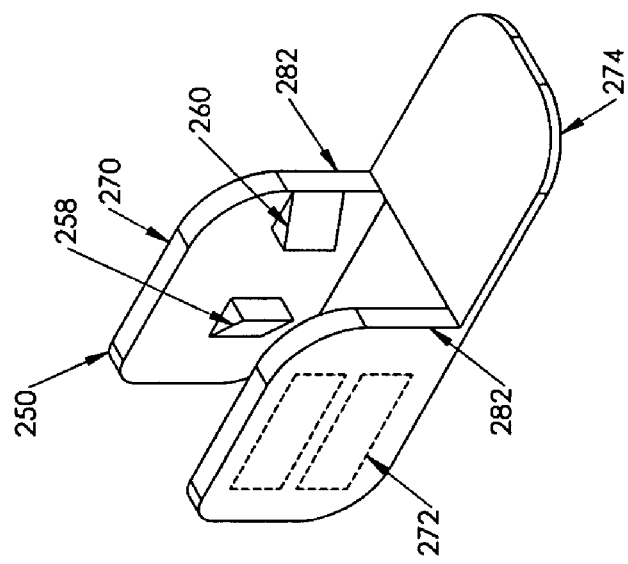

An additional embodiment of indicia-bearing device 250 is illustrated in FIGS. 18 and 19. As with device 200, device 250 is also adapted to clip directly onto clamp 40. Device 250 is similar to device 200, and has three indicia-bearing surfaces on walls 270, 272, 274, and pairs of latches 258, 260 for clipping onto clamp 40 at end 49. With device 250, the side walls 270, 272 are joined only at first ends 282 by wall 274. Both devices 200 and 250 provide substantial viewability of the length of tube 38 disposed within clamp 40, as is desired.

Referring now to FIGS. 20 to 22, indicia-bearing device 300 is shown to be adapted to latch onto a clamp 330 that is identical to clamp 40 of the previous Figures, but that will be now be explained in greater detail. Device 300 is shown to provide a single large indicia-bearing surface 320 that upon assembly to clamp 330 extends along the bottom 332 of clamp 330 from first clamp end 334 to the opposite second clamp end 336. Device body 302 includes opposite ends that are slightly curved upwardly to complement the adjacent curved outer surfaces of clamp 330. Along the inner (or top) surface of body 302, the connecting section comprises a pair of opposing latch members 308, 310 that have free ends that extend toward each other. Latch members 308, 310 are associated with openings 338, 340 of clamp member 330 at respective first and second clamp ends 334, 336 through which the tubing 38 extends. (The tubing is not shown in these Figures in order to provide for clearly viewing the latching system of the device with respect to the clamp.) Device 300 can be clipped onto the clamp by sequentially latching the latch members 308, 310 through the associated clamp openings 338, 340 at their respective bottom peripheral portions 342, 344, easily accomplished in view of the flexibility of the device body 302, and that of the clamp 330. The latch members are designed and dimensioned so that there is no impingement on the tubing that extends through clamp openings 338, 340, which conventionally are manufactured to be larger than the outer diameter of the tubing with which the clamp is to be used.

Figure 24:
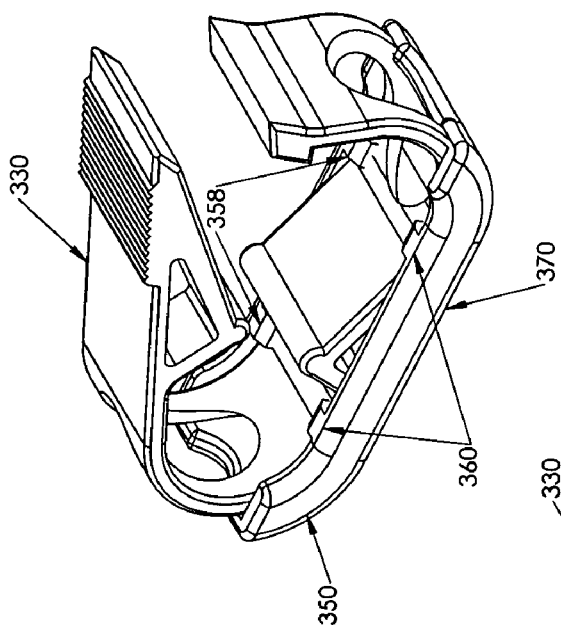
FIGS. 23 to 25 are isometric views of an additional embodiment of indicia-bearing device by itself and as secured to a clamp member as seen from two different angles.
Figure 25:
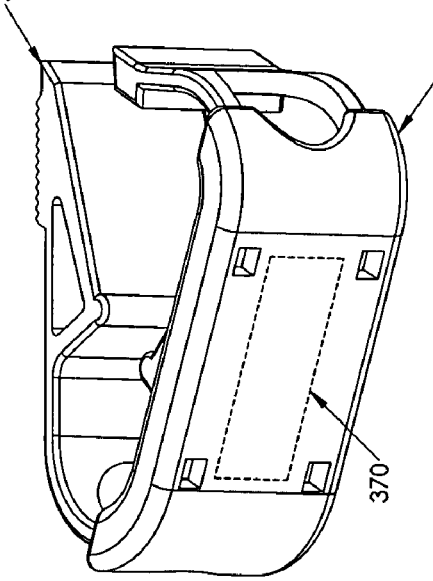
Figure 23:
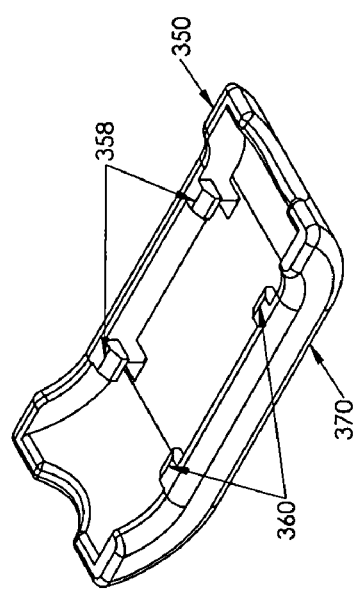

FIGS. 23 to 25 illustrate an indicia-bearing device 350 that is similar to device 300 of FIGS. 20 to 22. Device 350 includes an indicia-bearing surface 370 that will be positioned along the bottom of the clamp when clipped thereto. The connection section comprises two pairs of opposing latch projections 358, 360 that are adapted to latch to side edges 346, 348 of clamp 330 (FIG. 20).

Figure 27:
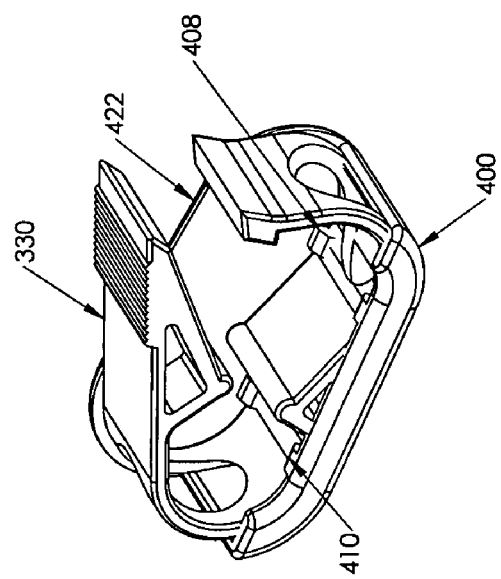
FIGS. 26 to 28 are isometric views and a bottom view of an additional embodiment of indicia-bearing device by itself and as secured to a clamp member.
Figure 28:
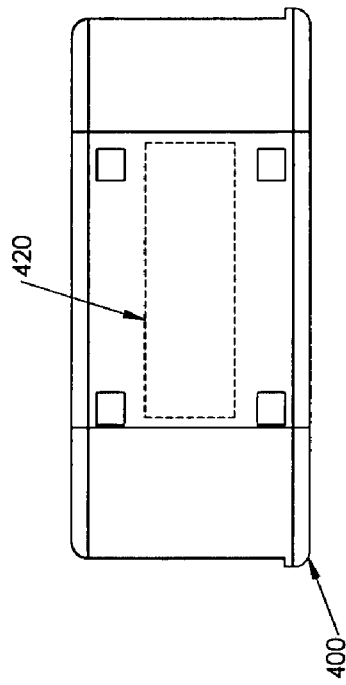
Figure 26:
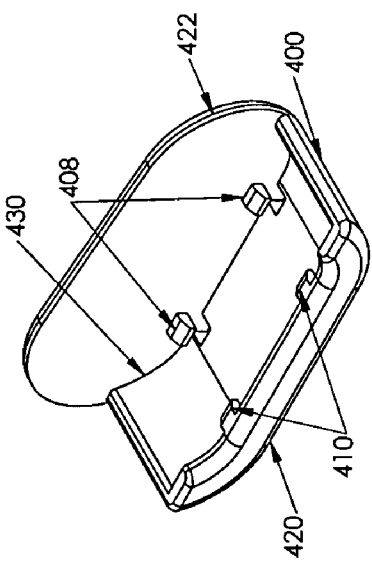

Another embodiment of indicia-bearing device 400 is shown in FIGS. 26 to 28, similar to the device 350 of FIGS. 23 to 25. Device 400 has two pairs of latch projections 408, 410 that latch onto side edges 346, 348 of clamp 330 (FIG. 20). In addition to an enlarged indicia-bearing surface 420 that extends along the bottom of clamp 330, device 400 further includes a second wall having an outwardly facing indicia-bearing surface 422 that projects upwardly from a side edge 430 of surface 420 and along the side of clamp 330. It is seen that indicia may be placed on both surfaces of the upwardly projecting wall, since the inwardly facing surface indicia may be viewed through the clamp and transparent tubing.

Figure 30:
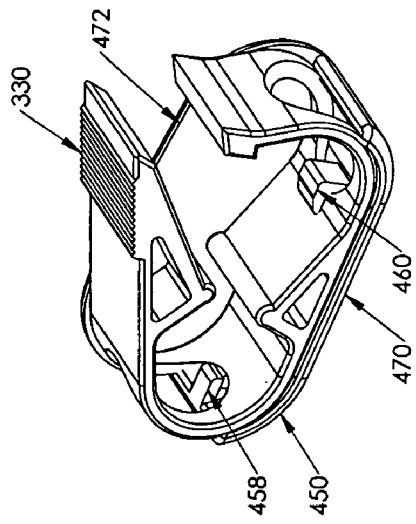
FIGS. 29 to 31 are isometric views of an additional embodiment of indicia-bearing device by itself and as secured to a clamp member seen from two different angles.
Figure 31:
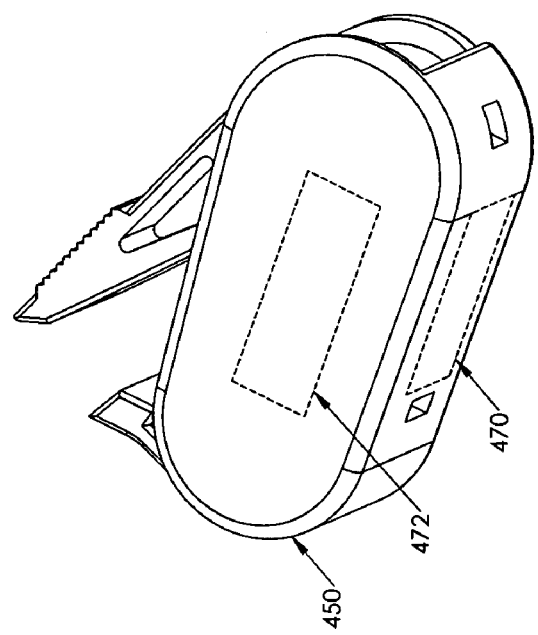
Figure 29:
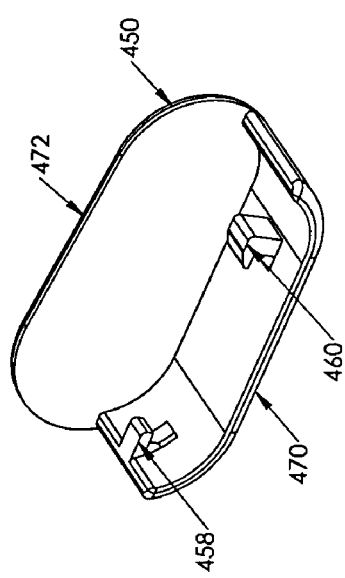

In FIGS. 29 to 31 is seen an indicia-bearing device 450 in which the device 450 includes a first and second indicia-bearing surfaces 470, 472 as with device 400 of FIG. 23. The connection section is defined by first and second latch projections 458, 460 that include free ends extending toward each other along the inwardly facing (top) surface of indicia-bearing surface 470, which are like the latch projections described with respect to device 300 of FIGS. 20 to 22, and that latch onto opening peripheries 342, 344 of clamp 330 (FIG. 20).

Figure 33:
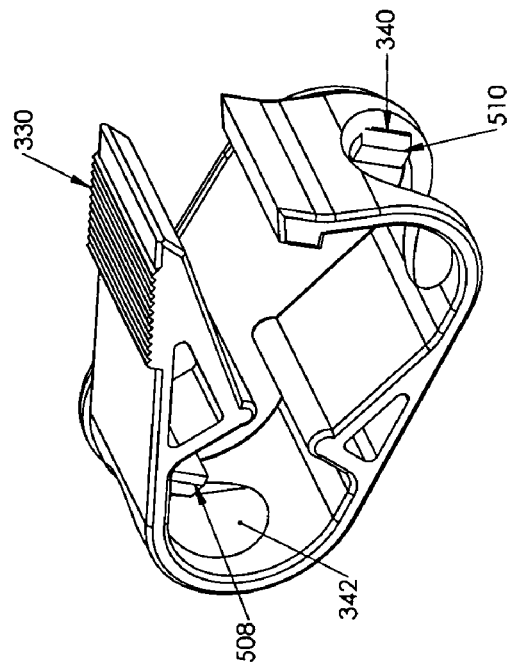
FIGS. 32 to 34 are isometric views and a bottom view of yet another embodiment of indicia-bearing device by itself and as secured to an assembly of a flexible tube and a clamp member.
Figure 34:
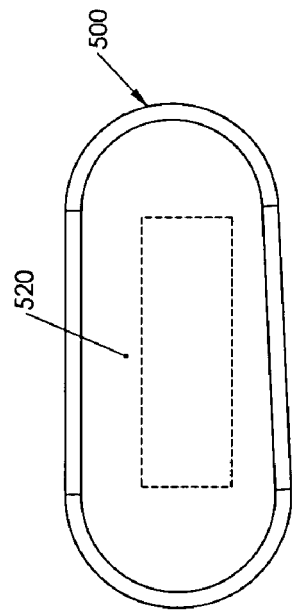
Figure 32:
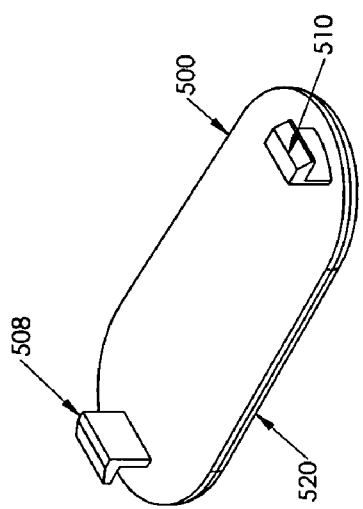

Now with regard to indicia-bearing device 500 of FIGS. 32 to 34, device 500 is provided with a pair of latch projections 508, 510 at respective ends of the inwardly facing surface of indicia-bearing surface 520 and that are seen to generally extend away from each other. Device 500 is clipped to clamp 330 along either side thereof by latching onto side peripheries of openings 340, 342 (see FIG. 20).

Indicia-bearing device 550 of the present invention is illustrated in FIGS. 35 to 37 and is rather box-shaped and adapted to be clipped directly to flexible tube 38, which is shown having a clamp 40 and fittings at both the proximal and distal ends that altogether form an extension tube assembly. Device 550 has a body 552 that defines a C-shaped channel 554 therealong, such that the flexible tube 38 can be urged into the entrance 558 of the C-shaped channel from laterally thereof. Device 550 is shown to have two indicia-bearing surfaces 570, 572 orthogonal to each other at the corner opposed from the C-shaped channel entrance 558. Smaller outwardly facing surfaces 574, 576 are also provided that may also be used to bear indicia thereon. Corners 580 are shown as being fluted therealong.

Figure 38:
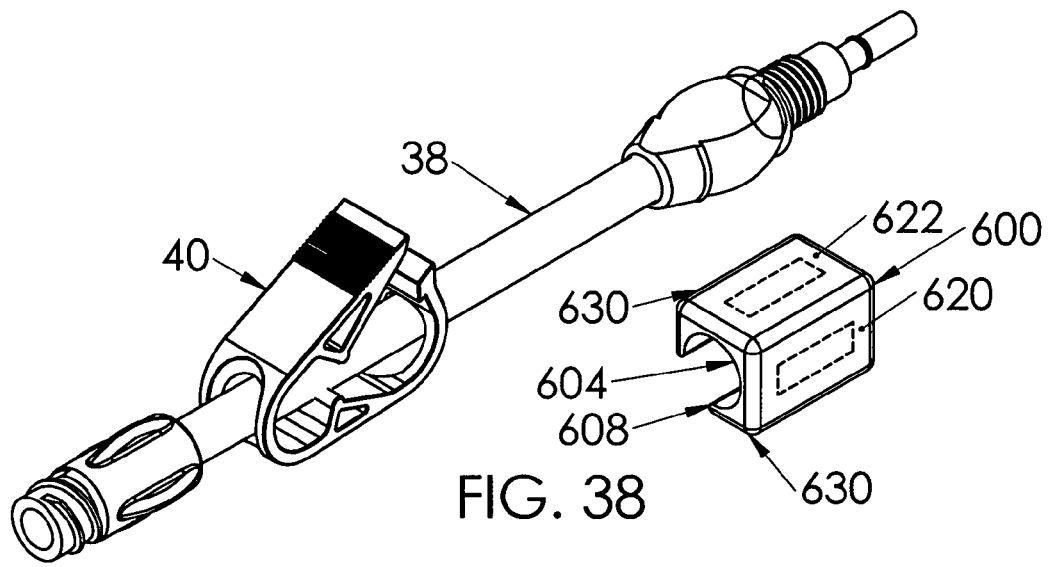
FIGS. 38 and 39 are isometric views of still another embodiment of indicia-bearing device spaced from and secured to a flexible tube, respectively, similar to that of FIGS. 36 and 37.
Figure 39:
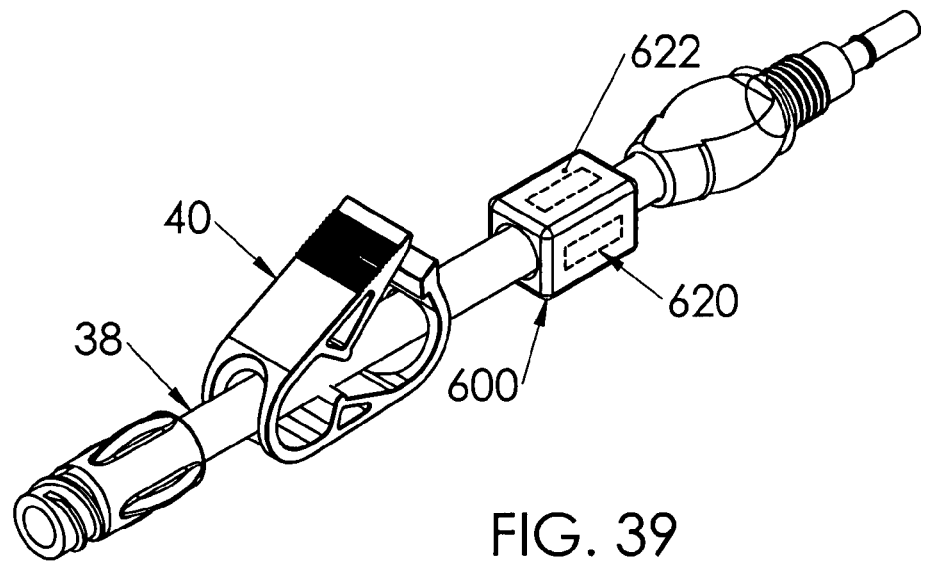

In FIGS. 38 and 39, indicia-bearing device 600 is shown that is similar to device 550 of FIGS. 35 to 37. Device 600 is also box-shaped and includes two adjoining indicia-bearing surfaces 620, 622, similar to device 550 of FIGS. 35 to 37 and has a C-shaped channel 604 therealong with a tube-receiving entrance 608. The corners 630 are not fluted.

Figure 40:
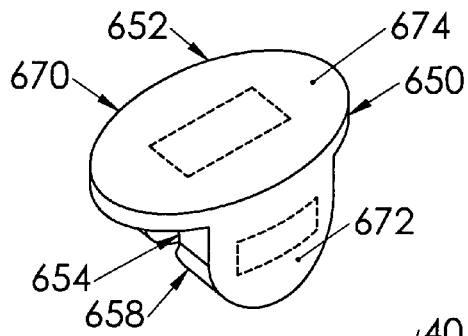
FIGS. 40 to 42 are isometric views of still another embodiment of indicia-bearing device by itself and as secured to a flexible tube.
Figure 41:
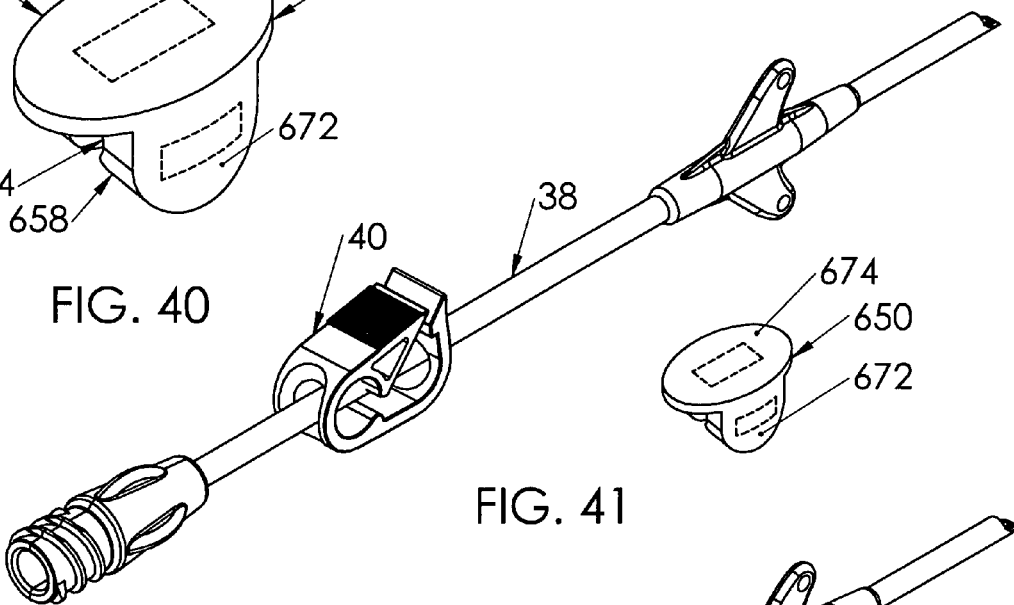
Figure 42:
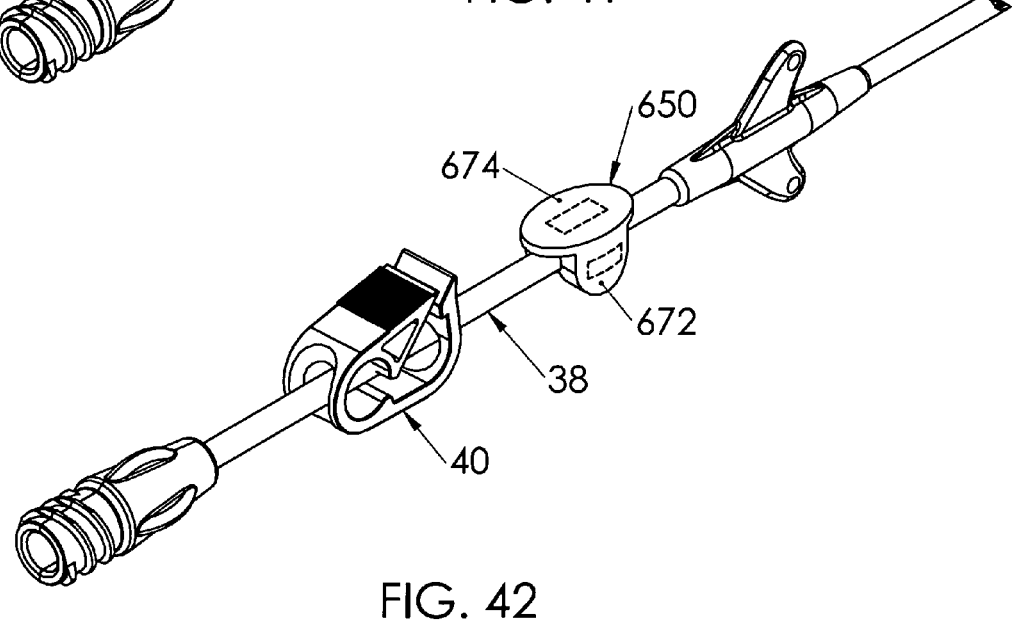

With regard to FIGS. 40, 41 and 42, indicia-bearing device 650 is seen that again is adapted to be clipped directly to flexible tubing as with devices 550 and 600. Device 650 has a body 652 that defines therealong a C-shaped channel 654 having a tube-receiving entrance 658, being applied from laterally of the tube 38. Device has three outwardly facing indicia-bearing surfaces 670, 672, 674 being disposed about the body 652 arranged with two opposite sides and one side adjoining the two opposite sides of the body. Indicia-bearing surface 674 is seen to be larger than surfaces 670, 672 and may contain more information as a result. The indicia-bearing surfaces are seen to have substantially rounded peripheries.

A further embodiment of indicia-bearing device 700 of the present invention is illustrated in FIGS. 43 to 45. Device 700 is similar to device 650 of FIGS. 40 to 42 with a C-shaped channel 704 and three enlarged outwardly facing indicia-bearing surfaces 720, 722, 724, and is clippable directly to flexible tubing 38.

Figure 46:
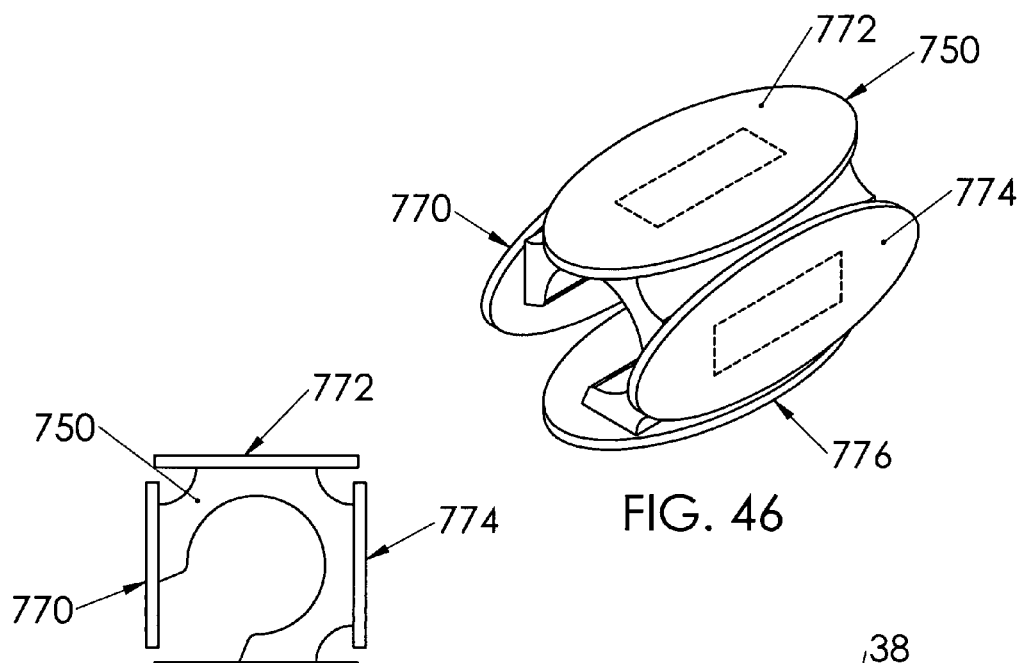
FIGS. 46 to 48 are isometric views of yet another embodiment of indicia-bearing device by itself and as secured to a flexible tube.
Figure 47:
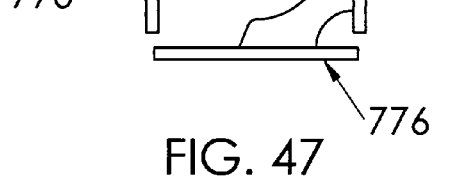
Figure 48:
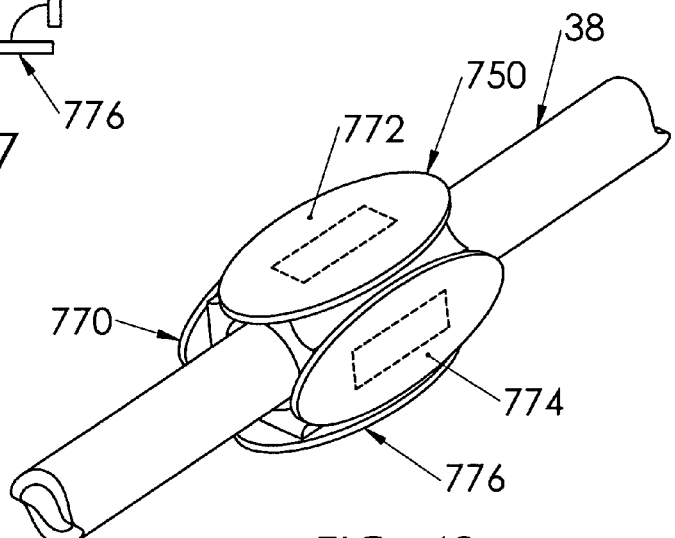
Figure 49:
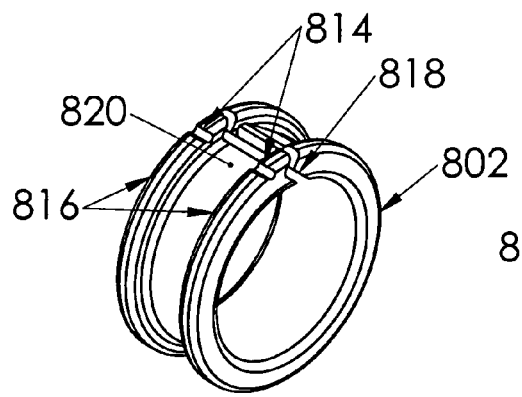
FIGS. 49 to 53 are isometric views of an additional embodiment of indicia-bearing device by itself, having an indicia-bearing strap, and as assembled in elevation and isometric views, and an alternative printed label, respectively.
Figure 50:
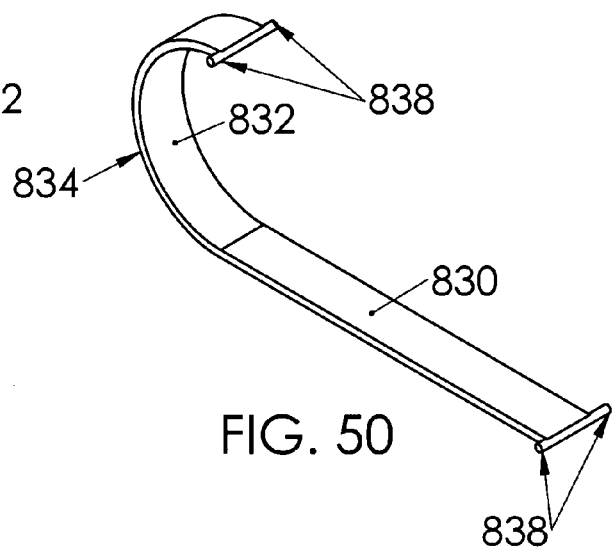
Figure 51:
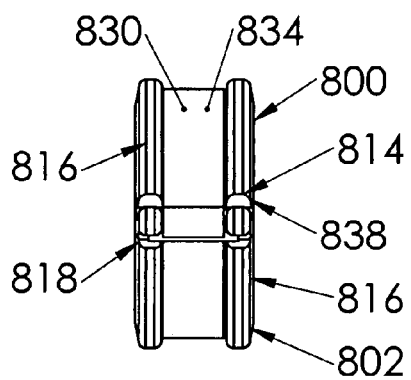
Figure 52:
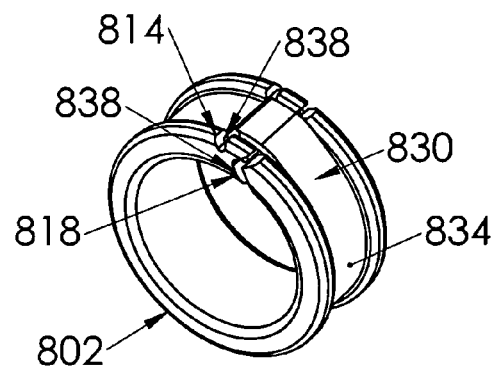
Figure 53:
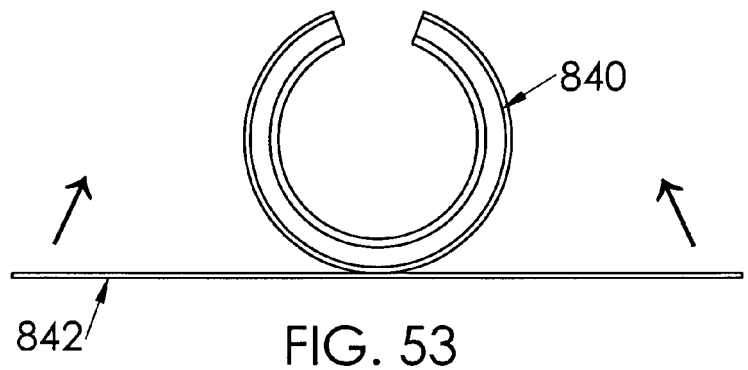

FIGS. 46 to 48 present another embodiment of indicia-bearing device 750 of the present invention. Device 750 is seen to be similar to device 700 of FIGS. 43 to 45 and has four enlarged outwardly facing indicia-bearing surfaces 770, 772, 774, 776 facing different directions that are orthogonal with each other so that information is viewable from practically any angle around the tubing.

Regarding FIGS. 49 to 53, indicia-bearing device 800 is shown to be ring-shaped and clippable about a flexible tubing at a selected location therealong. Device 800 includes a body 802 that is of sufficient width to bear indicia on its outwardly facing surface 820 that is readable about its circumference, or a body 840 to have a label 842 (FIG. 53) pre-adhered thereto that contains the indicia. A strap 830 may be positioned and fastened to extend around the outwardly facing circumference of body 802 that would be providable with indicia thereon, having a width comparable to that of body 802; optionally, both sides 832, 834 of the strap may bear indicia such that either side may face outwardly upon being placed around device 800. Device body 802 is annular of an inner diameter to fit around the tubing without impinging thereon but also, preferably, not be freely translatable therealong, with two adjacent ends completing the annulus; body 802 has sufficient elasticity to be temporarily flexed to be opened when being placed about the tubing and may simply have enough rigidity to remain in the annular shape; body 802, alternatively may have a connecting section at each end for self-connection about the tubing. Strap 830 includes a connecting section whereby the strap is securable about body 802, which may cooperate with complementary structure of body 802 or the ends of the strap may be self-connecting (not shown). Strap 830 may be of moderately elastic material such as polyurethane such as PELLATHANE® resin and have pin sections 838 extending laterally outwardly from each end of the strap to cooperate with corresponding appropriately shaped notches 814 (FIG. 51) in upstanding side wall portions 816 of body 802, or be held at one end beneath a latch projection 818 as shown. Or, strap 830 may be of elastic material such as of isoprene resin and be thick enough to have rigid plastic pins extending transversely through holes adjacent the ends thereof (not shown). The upstanding side wall portions 816 restrain the strap therebetween from any lateral movement. Optionally, the strap may be wrapped about body 802 more than once.

Indicia-bearing device 850 is depicted in FIGS. 54 to 57 is similar to device 800 of FIGS. 49 to 53. Again, either the outwardly facing circumferential surface of body 852 may bear indicia, or a strap 830 (FIG. 50) may be used as with device 800; optionally, an indicia-bearing label strip 842 (FIG. 53) pre-adhered to the body 852 may be used. A magnifying component 890 is shown to be positioned atop the indicia-bearing outwardly facing indicia-bearing surface of body 852 or the strap 830 to enhance the readability of the indicia thereon. The magnifying component, or magnifier, may be of transparent plastic such as polyacrylate, and have a shape in cross-section that is convex outwardly to define a lens. The magnifying component 890 is annular, with two adjacent, preferably beveled and overlapping ends 892, 894 completing the annulus, and has sufficient elasticity to be temporarily flexed; the magnifying component 890 may have a connecting section as with strap 830 or may simply have enough rigidity to remain in the annular shape about the device 850.

Generally, with respect to all of the disclosed embodiments, the indicia-bearing devices may be made of ABS, polyvinyl chloride, polypropylene or other suitable plastic materials. The clamp members may be made of similar suitable plastic materials. The flexible tubing may be biocompatible elastomers such as silicone rubber, usually for catheters, or polyurethane, usually for extension tubing or some catheters; however, these materials are not limiting to the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An information-bearing article for use with and assembly to a tubing assembly, the tubing assembly having a length of flexible tubing and a clamp, where the clamp is affixed to the tubing and disposed therealong and when so affixed is operable between an unclamping state and a clamping state occluding the flexible tubing, comprising:

a body having at least one wall defining an outwardly facing surface bearing indicia thereon, the body further having a connecting section adapted to enable the body to be affixed to a clamp of the tubing assembly such that the body is exterior of the clamp, wherein the connecting section of the body comprises at least a pair of latch projections that are associated with portions of the clamp accessible from laterally of the clamp, that are latchable to the clamp, and wherein the body is so configured such that the body is substantially adjacent to outer surfaces of the clamp, and not thereafter interfering with operability of the clamp between its clamping and unclamping states, and without impinging on the tubing.

2. The information-bearing article of claim 1, wherein the body is adapted to be removable from the clamp while the clamp remains disposed along and about the tubing.

3. The information-bearing article of claim 1, wherein the body is made of somewhat flexible material.

4. The information-bearing article of claim 1, wherein the latch projections coextend from a common inwardly facing surface of the body.

5. The information-bearing article of claim 4, wherein the latch projections include free ends that generally extend away from each other.

6. The information-bearing article of claim 4, wherein the body has a single wall having a shape generally complementary to a side profile of the clamp adjacent thereto.

7. The information-bearing article of claim 1, wherein the body includes at least one transverse section extending between opposing sides of the body relative to the tubing.

8. The information-bearing article of claim 7, wherein the body includes opposing side wall portions coextending from the at least one transverse section, the opposing side wall portions having outwardly facing surfaces at least one of which is an indicia-bearing surface.

9. The information-bearing article of claim 7, wherein the body includes a second wall adjacent to the at least one wall and joined longitudinally to an edge thereof and orthogonal thereto, the second wall defining a second outwardly facing surface defining a second indicia-bearing surface.

10. The information-bearing article of claim 1, wherein the body defines at least one generally planar outwardly facing surface bearing indicia thereon.

11. The information-bearing article of claim 10, wherein the periphery of the at least one generally planar outwardly facing indicia-bearing surface is generally rectangular.

12. The information-bearing article of claim 10, wherein the periphery of the at least one generally planar outwardly facing indicia-bearing surface is partially rounded or circular.

13. The information-bearing article of claim 1, wherein the body defines at least two generally planar outwardly facing surfaces bearing indicia thereon.

14. The information-bearing article of claim 1, wherein the body defines at least three generally planar outwardly facing surfaces bearing indicia thereon.

15. The information-bearing article of claim 14, wherein two of the generally planar outwardly facing surfaces are defined on opposing side walls of the body, and the third extends at one end of the body from ends of edges of both opposing side walls and away therefrom.

16. The information-bearing article of claim 1, wherein the body includes at least one side wall shaped generally complementarily to a side profile of the clamp adjacent thereto.

17. An information-bearing article for use with and assembly to a tubing assembly, the tubing assembly having a length of flexible tubing and a clamp, where the clamp is affixed to the tubing and disposed therealong and when so affixed is operable between an unclamping state and a clamping state occluding the flexible tubing, comprising:

a body having at least one wall defining an outwardly facing surface bearing indicia thereon, the body further having a connecting section adapted to enable the body to be affixed to a clamp of the tubing assembly such that the body is exterior of the clamp, the body being so configured such that the body is substantially entirely adjacent to outer surfaces of the clamp while not traversing interiorly of the clamp nor thereafter interfering with operability of the clamp between its clamping and unclamping states, and without impinging on the tubing, wherein the body includes at least one transverse section extending between opposing sides of the body relative to the tubing, wherein the body includes opposing side wall portions coextending from the at least one transverse section, the opposing side wall portions having outwardly facing surfaces at least one of which defines an indicia-bearing surface, and wherein the body includes two pairs of latch projections that are associated with portions of the clamp and that are latchable thereto.

18. The information-bearing article of claim 17, wherein the two pairs of latch projections coextend from respective inwardly facing surfaces of the opposing side wall portions of the body.

19. The information-bearing article of claim 17, wherein the body defines one said transverse wall section and wherein said one indicia-bearing side wall portion has a shape generally complementary to a side profile of the clamp adjacent thereto.

20. The information-bearing article of claim 19, wherein the other of said opposing side wall portion extends only a limited distance from said transverse wall section, wherein said two pairs of latch projections extend toward each other proximate the transverse section, wherein one said pair of latch projections is defined on an inwardly facing surface of said one indicia-bearing side wall, and the other of said pair of latch projections is defined on an inwardly-facing surface of the other side wall portion.

21. The information-bearing article of claim 19, wherein the transverse wall section has ends that are slightly curved to complement curved exterior surface portions of the clamp adjacent thereto.

22. An information-bearing article for use with and assembly to a tubing assembly, the tubing assembly having a length of flexible tubing and a clamp, where the clamp is affixed to the tubing and disposed therealong and when so affixed is operable between an unclamping state and a clamping state occluding the flexible tubing, comprising:

a body having at least one wall defining an outwardly facing surface bearing indicia thereon, the body further having a connecting section adapted to enable the body to be affixed to a clamp of the tubing assembly such that the body is exterior of the clamp, the body being so configured such that the body is substantially entirely adjacent to outer surfaces of the clamp while not traversing interiorly of the clamp nor thereafter interfering with operability of the clamp between its clamping and unclamping states, and without impinging on the tubing, wherein the connecting section of the body comprises at least a pair of latch projections that are associated with portions of the clamp accessible from laterally of the clamp, that are latchable to the clamp, and wherein the latch projections coextend from a common inwardly facing surface of the body and include free ends that generally extend toward each other.

23. The information-bearing article of claim 22, wherein the body has at least one wall having ends that are slightly curved to complement curved exterior surface portions of the clamp adjacent thereto.

24. The information-bearing article of claim 23, wherein at least one of the pair of latch projections is defined on one of said ends of said at least one wall to extend toward the other of said pair of latch projections.

25. The information-bearing article of claim 23, wherein the body includes a second wall extending orthogonally from a side edge of said at least one wall and defining an indicia-bearing surface.

26. The information-bearing article of claim 25, wherein the second wall is shaped to complement generally a side profile of the clamp adjacent thereto.

27. An information-bearing article for use with and assembly to a tubing assembly, the tubing assembly having a length of flexible tubing and a clamp, where the clamp is affixed to the tubing and disposed therealong and when so affixed is operable between an unclamping state and a clamping state occluding the flexible tubing, comprising:

a body having at least one wall defining an outwardly facing surface bearing indicia thereon, the body further having a connecting section adapted to enable the body to be affixed to a clamp of the tubing assembly such that the body is exterior of the clamp, the body being so configured such that the body is substantially entirely adjacent to outer surfaces of the clamp while not traversing interiorly of the clamp nor thereafter interfering with operability of the clamp between its clamping and unclamping states, and without impinging on the tubing, wherein the body includes a transverse section extending between opposing sides of the body relative to the tubing, wherein the body includes opposing side wall portions coextending from the transverse section having outwardly facing surfaces at least one of which defines an indicia-bearing surface, and wherein the transverse section defines a C-shaped channel adapted to secure the body about the tubing adjacent to the clamp at an end thereof, and further includes a pair of opposing latching projections extending inwardly from respective inwardly facing surfaces of side walls of the body and spaced from the transverse section to cooperate with framework of the clamp to secure the body against translation along the tubing away from the clamp.

28. A combination of a clamp, flexible tubing and an information-bearing article, where the clamp is disposable along a length of the tubing and affixable thereto and when so affixed is operable between an unclamping state and a clamping state occluding the flexible tubing, comprising:

a length of flexible tubing;

a clamp component affixable to the flexible tubing and including a clamping section that is manipulatable between clamping and unclamping states with respect to the flexible tubing; and an initially separate body having at least one outwardly facing surface bearing indicia thereon, the body further having a connecting section enabling the body to be affixed to the clamp such that the body is exterior of the clamp, the body being so configured such that the body is substantially entirely adjacent to outer surfaces of the clamp while not traversing interiorly of the clamp nor thereafter interfering with operability of the clamp between clamping and unclamping states, and without impinging on the tubing wherein the body includes at least one transverse section extending between opposing sides of the body relative to the hinge.

29. An information-bearing article for use with and assembly to a tubing assembly, the tubing assembly having a length of flexible tubing and a clamp, where the clamp is affixed to the tubing and disposed therealong and when so affixed is operable between an unclamping state and a clamping state occluding the flexible tubing, comprising:

a body having at least one wall defining an outwardly facing surface bearing indicia thereon, the body further having a connecting section adapted to enable the body to be affixed to a clamp of the tubing assembly such that the body is exterior of the clamp, the body being so configured such that the body is substantially entirely adjacent to outer surfaces of the clamp while not traversing interiorly of the clamp nor thereafter interfering with operability of the clamp between its clamping and unclamping states, and without impinging on the tubing, wherein the body includes a transverse wall section extending between opposing sides of the body relative to the tubing, wherein the body includes opposing side wall portions coextending from the at least one transverse section each having outwardly and inwardly facing surfaces, and wherein the body includes two pairs of latch projections defined on respective inwardly facing surfaces of the opposing side wall portions that are associated with portions of the clamp and that are latchable to the clamp.

30. The information-bearing article of claim 29, wherein the transverse wall section has ends that are slightly curved to complement curved exterior surface portions of the clamp adjacent thereto.

* * * * *